(12) United States Patent
Liou et al.

(10) Patent No.: US 9,682,117 B2
(45) Date of Patent: Jun. 20, 2017

(54) **EXTRACT OF *ZINGIBER ZERUMBET* FOR RELIEVING SYMPTOMS OF DIABETIC RETINOPATHY**

(71) Applicant: HAN SHENG PHARMTECH, INC., Pingtung County (TW)

(72) Inventors: Shorong-Shii Liou, Pingtung (TW); I-Min Liu, Pingtung (TW)

(73) Assignee: Han Sheng Pharmtech, Inc., Pingtung, Pingtung County (TW)

( * ) Notice: Subject to any disclaimer, the term of this patent is extended or adjusted under 35 U.S.C. 154(b) by 148 days.

(21) Appl. No.: 14/632,586

(22) Filed: Feb. 26, 2015

(65) Prior Publication Data

US 2016/0250275 A1    Sep. 1, 2016

(51) Int. Cl.
*A61K 36/906* (2006.01)
*A61K 36/9068* (2006.01)

(52) U.S. Cl.
CPC .... *A61K 36/9068* (2013.01); *A61K 2236/333* (2013.01)

(58) Field of Classification Search
None
See application file for complete search history.

(56) References Cited

U.S. PATENT DOCUMENTS

| 5,925,615 A * | 7/1999 | Kern | A61K 8/97 424/74 |
| 2004/0234633 A1 | 11/2004 | Kim et al. | |
| 2006/0083799 A1* | 4/2006 | Chaung | A61K 36/9068 424/756 |
| 2011/0300246 A1 | 12/2011 | Huang | |

OTHER PUBLICATIONS

Yob et al. (2011) Evidence-Based Complementary and Alternative Medicine, Volum 2011, Article ID 543216, 12 pages.*

* cited by examiner

Primary Examiner — Chris R Tate
Assistant Examiner — Russell Fiebig
(74) Attorney, Agent, or Firm — Muncy, Geissler, Olds & Lowe, P.C.

(57) ABSTRACT

A method for manufacturing an extract of *Zingiber zerumbet*, which is used to manufacture the extract of *Zingiber zerumbet* for diabetic retinopathy, includes: soaking a raw sample of *Zingiber zerumbet* with vinegar for 8 hours; boiling the soaked product at 1.5-2.5 kg/m$^2$, 95-105° C. for 30 minutes to obtain a processed sample of *Zingiber zerumbet*; and extracting the processed sample of *Zingiber zerumbet* with an extractant being water or 95% ethanol at 70-90° C. for 8 hours to obtain the extract of *Zingiber zerumbet*. The present invention further relates to the extract of *Zingiber zerumbet* and a method for diabetic retinopathy by administrating the extract of *Zingiber zerumbet* to a subject in need.

3 Claims, 2 Drawing Sheets
(2 of 2 Drawing Sheet(s) Filed in Color)

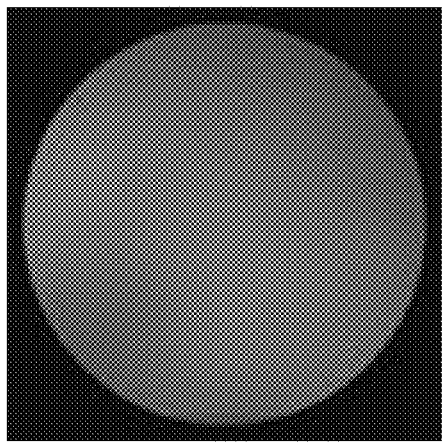 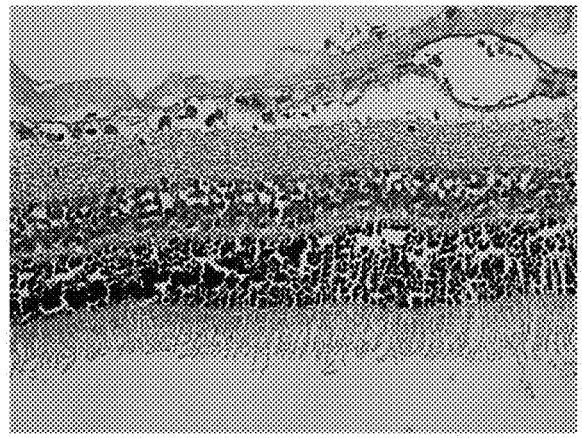
FIG. 1a　　　　　　　FIG. 1b
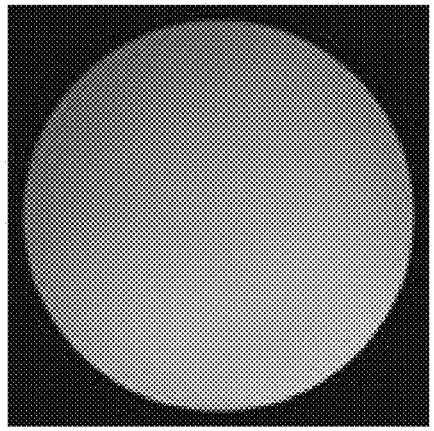 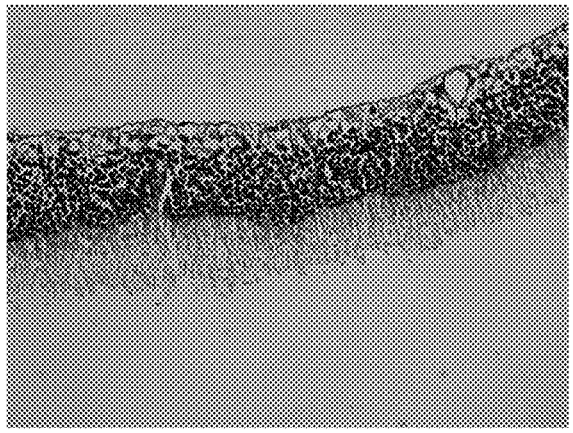
FIG. 2a　　　　　　　FIG. 2b
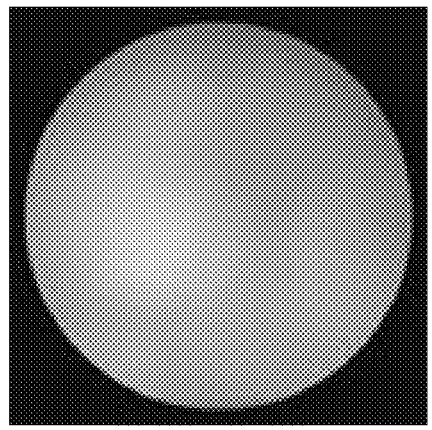 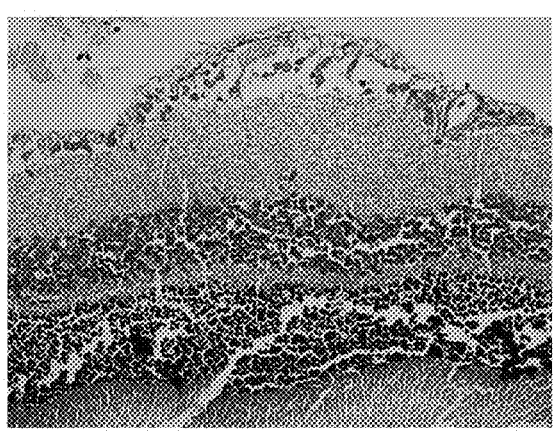
FIG. 3a　　　　　　　FIG. 3b

EXTRACT OF *ZINGIBER ZERUMBET* FOR RELIEVING SYMPTOMS OF DIABETIC RETINOPATHY

BACKGROUND OF THE INVENTION

1. Field of the Invention

The present invention relates to an extract of *Zingiber zerumbet* and, more particularly, to an extract of *Zingiber zerumbet* for diabetic retinopathy. The present invention further relates to a method for manufacturing the extract of *Zingiber zerumbet* and a method for diabetic retinopathy by administrating the extract of *Zingiber zerumbet* to a subject in need.

2. Description of the Related Art

Diabetic retinopathy is a complication of diabetes, which is caused by hyperglycemia-induced incompetence of the vascular walls, resulting in microvascular retinal changes, such as dysfunction of blood-retinal barrier and hyperpermeability of capillary circulation. Moreover, diabetic retinopathy is the leading cause of blindness in patients with diabetes.

Conventional methods for diabetic retinopathy include laser surgery, vitrectomy and intraocular injection of corticosteroids. However, all of the conventional methods belong to invasive treatments but cannot completely cure diabetic retinopathy. Therefore, patients with diabetic retinopathy have to monitor blood glucose level to adapt to maintain normal blood glucose level (euglycemia) all the time. Furthermore, intraocular injection of corticosteroids can also lead to side effects such as steroid-induced disorders. In light of this, it is necessary to improve the conventional method for diabetic retinopathy.

SUMMARY OF THE INVENTION

It is therefore the objective of this invention to provide a method for manufacturing an extract of *Zingiber zerumbet* for diabetic retinopathy.

It is another objective of this invention to provide an extract of *Zingiber zerumbet* for diabetic retinopathy.

It is yet another objective of this invention to provide a method for diabetic retinopathy without side effects lead by the conventional methods.

A method for manufacturing an extract of *Zingiber zerumbet* includes the steps of: soaking a raw sample of *Zingiber zerumbet* with vinegar for 8 hours; boiling the soaked product at 1.5-2.5 kg/m$^2$, 95-105° C. for 30 minutes to obtain a processed sample of *Zingiber zerumbet*; and extracting the processed sample of *Zingiber zerumbet* with an extractant being water or 95% ethanol at 70-90° C. for 8 hours to obtain the extract of *Zingiber zerumbet* for diabetic retinopathy.

In a preferred form shown, 5 kg of the raw sample of *Zingiber zerumbet* is soaked with 5 L of vinegar.

In a preferred form shown, 500 g of the processed sample of *Zingiber zerumbet* is extracted with 1 L of the extractant.

An extract of *Zingiber zerumbet* for diabetic retinopathy is manufactured by the method mentioned above.

A method for diabetic retinopathy includes administering the extract of *Zingiber zerumbet* to a subject in need thereof to relieve symptoms of diabetic retinopathy.

In a preferred form shown, the extract of *Zingiber zerumbet* is administered to the subject in need thereof in a dosage of 600 mg/per kilogram of body weight per day for 28 days.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given hereinafter and the accompanying drawings which are given by way of illustration only, and thus are not limitative of the present invention, and wherein:

FIG. 1*a* depicts a fundus photograph of rat (group C0) on day 28.

FIG. 1*b* depicts a PAS/Hematoxylin staining of rat (group C0) on day 28.

FIG. 2*a* depicts a fundus photograph of rat (group C1) on day 28.

FIG. 2*b* depicts a PAS/Hematoxylin staining of rat (group C1) on day 28.

FIG. 3*a* depicts a fundus photograph of rat (group C2) on day 28.

FIG. 3*b* depicts a PAS/Hematoxylin staining of rat (group C2) on day 28.

Figure 4A:
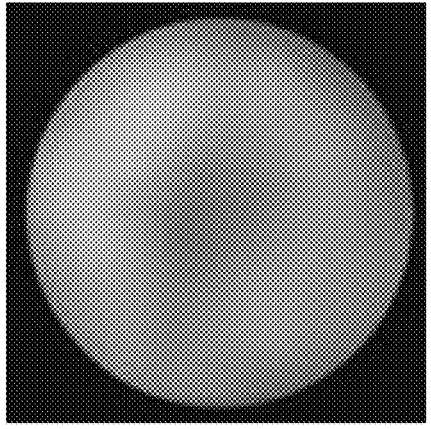
FIG. 4*a* depicts a fundus photograph of rat (group C3) on day 28.

In the various figures of the drawings, the same numerals designate the same or similar parts. Furthermore, when the term "first", "second", "third", "fourth", "inner", "outer" "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

An embodiment of an extract of *Zingiber zerumbet* according to preferred teachings of the present invention is extracted from a processed sample of *Zingiber zerumbet*. Moreover, before the extraction process, a raw sample of *Zingiber zerumbet* is soaked with vinegar and then boiled at a high temperature, and thus, flavonoids rich in the raw sample can be easily released in an extractant during the extraction process. Finally, the extract of *Zingiber zerumbet* rich in flavonoids is obtained, and can be used to recover the hyperglycemia-induced damages.

Specifically, the extract of *Zingiber zerumbet* can be manufactured as following: The raw sample is soaked with vinegar, followed by boiling at the high temperature to obtain the processed sample of *Zingiber zerumbet*. The processed sample is then extracted with the extractant to obtain the extract of *Zingiber zerumbet*.

In detail, the raw sample is rhizome, which is used as food flavoring and appetizers. Moreover, the rhizome can be used for toothache, indigestion, diarrhea, as well as increased circulation of the blood.

More particularly, the raw sample can be washed to remove impurities adhering on the surfaces of the raw sample, improving the processing process followed by. In this embodiment, the raw sample is placed in a sealed container to prevent from impurities entering into the sealed container during the soaking process, and therefore, vinegar can be penetrated into the raw sample. As an example, fresh rhizome (50 kg) is washed to remove the dust adhering on the surfaces, followed by slicing and air-drying to obtain the raw sample (5.3 kg) with moisture content of 89.4%. Moreover, the raw sample (5 kg) is then soaked with vinegar (5 L) for 8 hours to obtain a soaked product.

Consequently, the soaked product is placed in a pressure cooker, boiled at 1.5-2.5 kg/m$^2$, 95-105° C. for 30 minutes until the color thereof becoming dark brown to obtain the processed sample. The processed sample can further be freeze-dried to lower the moisture content (<10%) in order to prolong the shelf life of the processed sample.

The extraction process can be carried out by extracting the processed sample with the extractant chosen to be water or 95% ethanol to obtain the extract of Zingiber zerumbet, permitting flavonoids rich in the process sample releasing into the extractant. In this embodiment, the processed sample (500 g) is extracted with water or 95% ethanol (1 L) at 70-90° C. for 8 hours. The extraction process repeats for 3 times, and the resulting product is vacuum filtrated, vacuum concentrated, and freeze-dried to obtain the extract of Zingiber zerumbet.

The extract of Zingiber zerumbet according to the present invention can effectively recover the hyperglycemia-induced damages and relieve symptoms of diabetic retinopathy, thereby being potential to be applied to pharmaceutical industry, being an active ingredient of medication or health products for diabetic retinopathy. In the present invention, the extract of Zingiber zerumbet can be given to any subject in need individually or combined with any acceptable excipients, for example carriers or other ingredients, and is capable of being further manufactured into any form of medicament, such as pill, capsule, powder, solution and pastil for easy and convenient delivery to the subject in need.

In addition, the extract of Zingiber zerumbet can be administered to the subject in need thereof. For example, the extract of Zingiber zerumbet can be administered to the subject in need thereof in a dosage of 600 mg/per kilogram of body weight per day (600 mg/kg/day) for 28 days. Therefore, flavonoids rich in the extract of Zingiber zerumbet pose synergistic effect in the subject in need thereof, recovering the hyperglycemia-induced damages and relieving symptoms of diabetic retinopathy.

In order to evaluate the extract of Zingiber zerumbet poses effect on diabetic retinopathy, the following trials are carried out.

Trial (A): Manufacturing Procedure & Flavonoids Level.

Referring to TABLE 1, the extract of Zingiber zerumbet is manufactured as mentioned above. In detail, the raw sample of the processed sample (500 g) is extracted with the extractant (1 L), and the resulting product is vacuum filtrated, vacuum concentrated, and freeze-dried to obtain the extract of Zingiber zerumbet of groups A1-A4.

TABLE 1

| Groups | Sample | Extractant |
| --- | --- | --- |
| A1 | Raw sample | 95% ethanol |
| A2 | Raw sample | Water |
| A3 | Processed sample | 95% ethanol |
| A4 | Processed sample | Water |

For analyzing flavonoids, aluminium chloride solution (2%, 1 mL) is added into quercetin standards (1-100 mg/mL, 1 mL) or the extract of Zingiber zerumbet (1-100 mg/mL, 1 mL), respectively, followed by standing at room temperature for 10 minutes. The absorbance at 430 nm is then measured to determine flavonoids level of the extract of Zingiber zerumbet in a form of quercetin level per gram of the extract of Zingiber zerumbet.

TABLE 2

| Groups | Flavonoids level (mg/g) |
| --- | --- |
| A1 | 20.18 ± 1.87 |
| A2 | 10.16 ± 0.96 |
| A3 | 41.29 ± 2.13 |
| A4 | 21.85 ± 1.78 |

Referring to TABLE 2, by soaking the raw sample with vinegar and then boiling at a high temperature, flavonoids rich in the raw sample can be easily released in the extractant during the extraction process. Therefore, the extract of Zingiber zerumbet rich in flavonoids can be obtained.

Trial (B): Effects on Hyperglycemia-Induced Damages In Vitro.

ARPE-19 cells purchased from the Food Industry Research and Development Institute in Taiwan is used in trial (B). The ARPE-19 cells are cultured in DME/F-12 medium (1:1) containing sodium bicarbonate (1.2 g/L), $_L$-Glutamine (2.5 mM), HEPES (15 mM), sodium pyruvate (0.5 mM) and FBS (10%.) The ARPE-19 cells are incubated in an incubator with temperature of 37° C., $CO_2$ concentration of 5% and humidity of 95%. Medium used for culturing the ARPE-19 cells is renewed once in two days.

While subculturing, the ARPE-19 cells are centrifuged at 1,000 rpm for 5 minutes to remove supernatants, followed by mixing with fresh medium. The ARPE-19 cells preferably have a concentration of $1\times10^5$ to $1\times10^6$ cells/mL in 10 cm culturing dishes.

The culturing dishes 80 to 90% of bottom areas covered by the ARPE-19 cells are used in trial (B). Discolored medium is removed, PBS solution (8 mL) is used to wash the ARPE-19 cells and Trypsin/EDTA is added into the culturing dishes for 1-3 minutes. After the ARPE-19 cells dissociate with walls of the culturing dishes by slightly vortexing, the ARPE-19 cells are resuspended with prewarmed medium. The ARPE-19 cells are collected into centrifuge tubes, followed by centrifugation at 1,500 rpm for 10 minutes. Supernatants are removed and the ARPE-19 cells are resuspended in medium containing FBS. The ARPE-19 cells (20 μL) are collected, and trypan blue (20 μL) is added to the ARPE-19 cells for staining. The stained ARPE-19 cells are collected in cell counters, and numbers of the stained ARPE-19 cells are counted under microscope. Only the ARPE-19 cells with viability over 85% are suitable for the following experiments.

Concentrations of the ARPE-19 cells are adjusted to $1\times10^5$ cells/mL by medium containing FBS. The ARPE-19 cells are inoculated in a 96-well plate (100 μL, $1\times10^5$ cells/mL). The inoculated ARPE-19 cells are overnight cultured in an incubator with temperature of 37° C. and $CO_2$ concentration of 5%.

After culturing for 24 hours, a glucose solution (for final concentration of 6 mM) and the extracts of *Zingiber zerumbet* shown in TABLE 3 (100 μL, in a concentration of 1 mg/mL, dissolved in DMSO) are added into each well of the 96-well plate. The ARPE-19 cells are overnight cultured in an incubator with temperature being 37° C. and $CO_2$ concentration being 5%.

TABLE 3

| Groups | Glucose solution | Treatment |
|---|---|---|
| B0 | − | Water |
| B1 | + | Water |
| B2 | + | DMSO |
| B3 | + | The extract of *Zingiber zerumbet* of group A1 |
| B4 | + | The extract of *Zingiber zerumbet* of group A2 |
| B5 | + | The extract of *Zingiber zerumbet* of group A3 |
| B6 | + | The extract of *Zingiber zerumbet* of group A4 |

After culturing for 24 hours, medium is removed, and the ARPE-19 cells are washed by a PBS solution. 100 μL of CCK-8 containing-fresh medium is added into each well of the 96-well plate. The ARPE-19 cells react with CCK-8 for 2 hours in the incubator (37° C., 5% $CO_2$), followed by vortexing for 5 minutes. Absorbance of 450 nm of the ARPE-19 cells in each well is detected.

Survival rate of the ARPE-19 cells treated with the extracts shown in TABLE 4, while the survival rate is computed as followed:

Survival rate (%)=(Absorbance of a testing set/Absorbance of a control set)×100%

TABLE 4

| Groups | Survival rate (%) |
|---|---|
| B0 | 100.00 ± 2.96 |
| B1 | 54.27 ± 3.17 |
| B2 | 47.35 ± 2.58 |
| B3 | 55.26 ± 3.24 |
| B4 | 60.37 ± 4.21 |
| B5 | 93.37 ± 4.27 |
| B6 | 82.41 ± 4.61 |

Referring to groups B5 and B6 in TABLE 4, the extract of *Zingiber zerumbet* extracted from the processed sample pose activity of recovering the hyperglycemia-induced damages.

Trial (C): Effects on Diabetic Retinopathy In Vivo.

Wistar male rats (>8 week-old, weight 160-180 g) purchased from The National Laboratory Animal Center (NLAC) are used in trial (C). The rats are housed in an animal room in the Experimental Animal Center of Tajen university with constant temperature of 25±1° C., where is kept on a 12-hours light and 12-hours dark cycle. The rats are housed and kept on free diet and water.

Rats with type I diabetes (groups C0-C4 shown in TABLE 1) are induced by administration of streptozotocin (STZ, 60 mg/kg) via intraperitoneal injection after fasting for 72 hours. Moreover, after administration of STZ for 72 hours, the rats with type I diabetes show blood sugar level higher than 300 mg/L and symptoms including frequent urination, increased thirst and increased hunger.

Referring to TABLE 5, rats of groups C1-C4 are orally administered with the extract of *Zingiber zerumbet* of groups A1-A4 for 28 days, respectively. Intraocular pressure (IOP) on day 0 and day 28, and symptoms of diabetic retinopathy are monitored on day 28.

TABLE 5

| Groups | Treatment (dosage per day) |
|---|---|
| C0 | Water (1 mL/kg) |
| C1 | The extract of *Zingiber zerumbet* of group A1 (300 mg/kg) |
| C2 | The extract of *Zingiber zerumbet* of group A2 (300 mg/kg) |
| C3 | The extract of *Zingiber zerumbet* of group A3 (300 mg/kg) |
| C4 | The extract of *Zingiber zerumbet* of group A4 (300 mg/kg) |

The intraocular pressure of the rats of groups C0-C4 on day 0 and day 28 are monitored after anesthetizing with diethyl ether, respectively. Fundus photography is carried with MiiS Horus Scope DOC100 on day 28, after administrating of atropine (0.25%), followed by anesthetizing with diethyl ether. Furthermore, periodic acid-Schiff/Hematoxylin staining of retinal histologic specimens is carried out.

TABLE 6

Figure 4B:
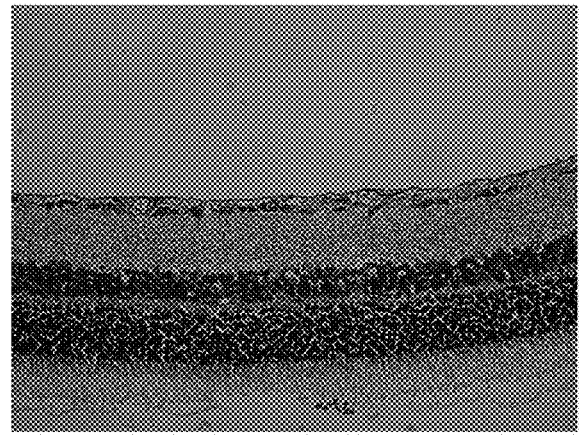
FIG. 4*b* depicts a PAS/Hematoxylin staining of rat (group C3) on day 28.
Figure 5A:
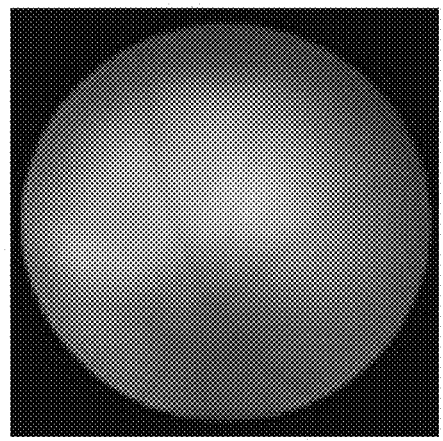
FIG. 5*a* depicts a fundus photograph of rat (group C4) on day 28.
Figure 5B:
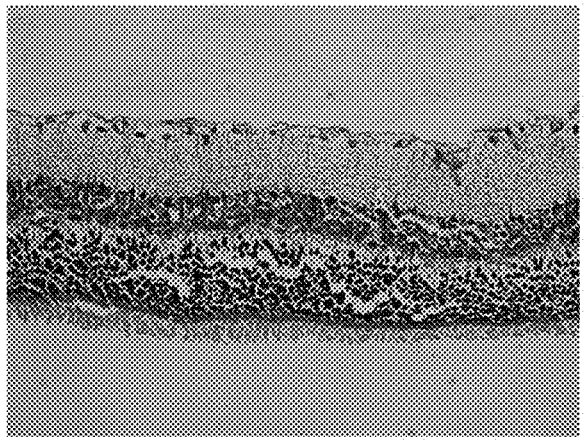
FIG. 5*b* depicts a PAS/Hematoxylin staining of rat (group C4) on day 28.

| | Intraocular pressure (mmHg) | | Fundus | PAS/Hematoxylin |
|---|---|---|---|---|
| Groups | Day 0 | Day 28 | photograph | staining |
| C0 | 19.52 ± 1.89 | 28.10 ± 3.15 | FIG. 1a | FIG. 1b |
| C1 | 20.17 ± 1.73 | 19.32 ± 2.73 | FIG. 2a | FIG. 2b |
| C2 | 19.82 ± 2.01 | 20.75 ± 2.67 | FIG. 3a | FIG. 3b |
| C3 | 19.17 ± 2.07 | 13.84 ± 2.87 | FIG. 4a | FIG. 4b |
| C4 | 20.31 ± 2.18 | 15.65 ± 3.70 | FIG. 5a | FIG. 5b |

As shown in TABLE 6, the IOP of group C0 on day 28 is higher than the IOP of group C0 on day 0, while the IOPs of groups C3 and C4 on day 28 are significantly lower than the IOPs of groups C3 and C4 on day 0. That is, the extract of *Zingiber zerumbet* extracted from the processed sample can effectively reduce the IOP of rats with type I diabetes. Moreover, the decrease of the IOP shows a positive correlation with flavonoids level of the extract of *Zingiber zerumbet* recorded in TABLE 2.

Moreover, newly formed blood vessels and bleeding on vitreous humour can be observed in FIG. 1a. In addition, accumulation of diffused fibrinogen-like protein covered on retinal, cell swelling, bleeding, vasodilation and angiogenesis can be observed in FIG. 1b. On the other hand, symptoms of diabetic retinopathy are relatively relieved in rats of groups C3 and C4, which is orally administered with the extract of *Zingiber zerumbet* extracted from the processed sample. That is, the extract of *Zingiber zerumbet* according to the present invention can be used to relieve symptoms of diabetic retinopathy.

In summary, by soaking the raw sample with vinegar and then boiling at a high temperature, flavonoids rich in the raw sample can be easily released in the extraction process. In such performance, the method according to the present invention can be used for manufacturing the extract of *Zingiber zerumbet* rich in flavonoids, which is capable of relieving symptoms of diabetic retinopathy.

Moreover, the extract of *Zingiber zerumbet* for diabetic retinopathy according to the present invention is rich in flavonoids, and therefore, the extract of *Zingiber zerumbet* can be used to slow or stop further vision loss.

Furthermore, the method according to the present invention is a more acceptable, non-invasive treatment, by administering the extract of *Zingiber zerumbet* rich in flavonoids, further preventing from side effects such as steroid-induced disorders.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for manufacturing an extract of *Zingiber zerumbet*, comprising the steps of:

soaking a raw sample of *Zingiber zerumbet* with vinegar for 8 hours to obtain a soaked product;

boiling the soaked product at 1.5-2.5 $kg/m^2$, 95-105° C. for 30 minutes to obtain a processed sample of *Zingiber zerumbet*; and extracting the processed sample of *Zingiber zerumbet* with an extractant selected from water or 95% ethanol at 70-90° C. for 8 hours to obtain the extract of *Zingiber zerumbet* wherein the extract is effective for relieving symptoms of diabetic retinopathy.

2. The method as claimed in claim 1, wherein 5 kg of the raw sample of *Zingiber zerumbet* is soaked with 5 L of vinegar.

3. The method as claimed in claim 1, wherein 500 g of the processed sample of *Zingiber zerumbet* is extracted with 1 L of the extractant.

* * * * *